United States Patent
Park et al.

(10) Patent No.: US 6,191,318 B1
(45) Date of Patent: Feb. 20, 2001

(54) PROCESS FOR PREPARING HYDROXYLATED AROMATICS BY HYDROGEN AND OXYGEN

(75) Inventors: Sang Eon Park; Chul Wee Lee; Jong San Chang; Yong Ki Park, all of Daejeon (KR)

(73) Assignee: Korea Research Institute of Chemical Technology (KR)

( * ) Notice: Under 35 U.S.C. 154(b), the term of this patent shall be extended for 0 days.

(21) Appl. No.: 09/332,135

(22) Filed: Jun. 14, 1999

(30) Foreign Application Priority Data

Jun. 15, 1998 (KR) .................................................. 98-22415

(51) Int. Cl.$^7$ .................................................. C07C 37/00
(52) U.S. Cl. ................................................ 568/802
(58) Field of Search ............................................. 568/802

(56) References Cited

U.S. PATENT DOCUMENTS 4,982,015 * 1/1991 Chao ..................................... 568/802
4,992,600 * 2/1991 Chao ..................................... 568/802

FOREIGN PATENT DOCUMENTS 5-320082 * 12/1993 (JP) .

* cited by examiner

Primary Examiner—Michael L. Shippen
(74) Attorney, Agent, or Firm—Finnegan, Henderson, Farabow, Garrett & Dunner

(57) ABSTRACT

The present invention relates to a process for preparing hydroxylated aromatics by using hydrogen and oxygen and more particularly, to a process for preparing hydroxylated aromatics by using hydrogen and oxygen with a two-component heterogeneous catalyst. One component consists of porous catalyst containing one of Group VIII B transition metals such as Pd, Pt, Au and Cu, and hydrogen transfer organic compounds such as anthraquinone. The other component consists of a catalyst containing a transition metal selected from Ti, V, and Sn with tetrahedral coordination geometry. The main advantages of this new catalytic system are to 1) overcome the drawbacks of liquid phase oxidation using conventional homogeneous catalysts, 2) avoid use of expensive hydrogen peroxide as an oxidant, and 3) improve the selectivity of the reaction.

13 Claims, No Drawings

PROCESS FOR PREPARING HYDROXYLATED AROMATICS BY HYDROGEN AND OXYGEN

BACKGROUND OF THE INVENTION

1. Field of the Invention

The present invention relates to a process for preparing hydroxylated aromatics by using hydrogen and oxygen and more particularly, to a process for preparing hydroxylated aromatics by using hydrogen and oxygen with a two-component heterogeneous catalyst. One component consists of porous catalyst containing one of Group VIII B transition metals such as Pd, Pt, Au and Cu, and hydrogen transfer organic compounds such as anthraquinone. The other component consists of a catalyst containing a transition metal selected from Ti, V, and Sn with tetrahedral coordination geometry. The main advantages of this new catalytic system are to 1) overcome the drawbacks of liquid phase oxidation using conventional homogeneous catalysts, 2) avoid use of expensive hydrogen peroxide as an oxidant, and 3) improve the selectivity of the reaction.

2. Description of the Related Art

Molecular oxygen ($O_2$), organic peroxide, and hydrogen peroxide have been used, in general, as selective oxidants for liquid phase oxidation of organic compounds.

A process for oxidation of benzene to phenol by using molecular oxygen as an oxidant has been disclosed. For example, benzene conversion rate is 15% and the selectivity towards phenol is approximately 70% in the presence of palladium supported on heteropolyacid catalyst in a pressure reactor at a temperature of 130° C. under 60 atmosphere of oxygen for 4 hours [*J. Mol. Catal. A.*, 1977, 120, 117]. To produce commercially available phenol, this reaction requires introduction of oxygen at high pressure which is dangerous to justify commercialization.

The process where organic peroxide such as cumen is used as an oxidant has been widely employed. But the process is uneconomical due to multi-steps of reaction and production of by-products such as acetone which causes environmental problem.

Due to above mentioned problems, hydrogen peroxide is preferred as an oxidant in the oxidation of organic compounds than molecular oxygen and organic peroxide. Hydrogen peroxide is very selective for the oxidation and decomposes to oxygen and water which are environmentally acceptable.

Processes for the introduction of a hydroxyl group onto the aromatic compounds have been reported. Followings are some examples.

A process for hydroxylation of aromatic hydrocarbons in the presence of Fe(II), ascorbic acid and EDTA at room temperature is disclosed. But it is not recommendable to apply this reaction for commercial exploitation due to extremely low yield [*J. Biol. Chem.*, 1954, 208, 731].

Another process for benzene hydroxylation to phenol is disclosed in which Fenton reagent comprising Fe(II) and hydrogen peroxide are used [*J. Am. Chem. Soc.*, 1975, 97, 363], therein active substance of Fenton reagent is hydroxyl radical derived from the reaction.

Another process for the hydroxylation of aromatic hydrocarbons by molecular oxygen is disclosed in the presence of metal ion such as Cu(I), Sn(II), Ti(III) or Fe(II)-EDTA of which standard oxidation/reduction electrode potential ($E_0$) is 0.15V.

In addition, a Cu—Pd incorporated silica catalyst has been known to be effective in the hydroxylation of benzene [*Catal. Lett.*, 1990, 4, 139]. In the process, reaction products are phenol and hydroquinone. In this reaction, Cu(I) reacts with oxygen in acidic condition to form hydrogen peroxide, which is reduced to hydroxyl radical to convert benzene to phenol in the reaction mixture. Cu(II), here, should be reduced to Cu(I) for this catalytic reaction, palladium-incorporated silica catalyst can be used to permit hydrogen reduction.

New type of molecular catalysts which incorporate titanium in the molecular framework such as titanium silicate (TS-1 zeolite) have been recently developed for the hydroxylation of aromatic compounds such as benzene and saturated hydrocarbons in the presence of hydrogen peroxide under mild conditions [*Appl. Catal.* 1990, 57, L1; *J. Mol. Catal.*, 1991, 68, 45]. TS-1 zeolite is a material with the structural features of ZSM-5 in which content of silicone is considerably high and Ti(IV) is coordinated as tetrahedral geometry in the framework at a low concentration of 0.1 to 2.5 mole %. Low content of titanium contributes to high dispersion of catalytic active site, resulting in the increase of oxidation selectivity. Reaction which employs TS-1 zeolite can be performed in 30% hydrogen peroxide aqueous solution under mild condition at a temperature of 20° C. to 100° C.

Because microporous zeolites have limitation for diffusion of large molecules, there is a need to develop and apply mesopore zeolite based catalyst that have larger pores.

Mesoporous Ti-MCM-41 shows lower conversion rate in the hydroxylation of small molecules such as 1-hexane when compared to the activity of TS-1 or Ti-β. However, Ti-MCM-41 shows higher selectivity than Ti-β in the oxidation of α-terpineol and norbornene. These results suggest that mesopore molecular sieves could be used for oxidation of large molecules.

Similar to the present invention, a two-component catalyst (Pd/C+TS-1) containing palladium and titanium has been applied for the hydroxylation of benzene with hydrogen and oxygen at atmospheric pressure at 35 ° C. [*J. Chem. Soc. Chem. commun.* 1992, 1446], but this reaction has drawback of low reactivity.

A silica catalyst containing both copper and palladium has also been utilized to oxidize benzene with hydrogen and oxygen under atmospheric pressure and at a temperature of 50° C. [*JCS Perkin Trans.* 2, 1990, 1991], but this reaction has the maximum turnover number of about 3.8.

As mentioned above, direct oxidation of benzene to phenol by hydrogen peroxide has numerous problems which include the following: (1) high costs of hydrogen peroxide; (2) low stability due to the impurities derived from the process of preparation of hydrogen peroxide; (3) difficulties in storage and transport. Therefore, it can be suggested that an oxidation process that utilizes reaction with hydrogen and oxygen, instead of hydrogen peroxide, and conducted at mild reaction conditions would be more environmentally acceptable.

SUMMARY OF THE INVENTION

The inventors of this invention have investigated for direct hydroxylation of aromatic hydrocarbons by hydrogen and oxygen under mild condition without direct introduction of expensive hydrogen peroxide during the oxidation process. As a result, these inventors have developed the method of direct production of hydrogen peroxide using porous zeolite catalyst which contains Group VIII transition metal and alkylanthraquinone and its derivative as hydrogen transfer compound [Korea Patent Appln. No. 97-50302]. Based on the prior invention, the present inventors have now designed and prepared two-component heterogeneous catalyst, one of which is above-mentioned new porous catalyst which produces hydrogen peroxide from hydrogen and oxygen, instead of direct introduction of hydrogen peroxide, the other is a zeolite catalyst containing specific transition metal with tetrahedral coordination geometry which reacts with hydrogen peroxide to induce the effective oxidation.

The present invention, therefore, provides a process for preparing hydrogen peroxide from oxygen and hydrogen in-situ by means of newly designed and prepared two-component catalyst. Another object of this invention is to provide an improved process for preparing hydroxylated aromatic hydrocarbons with high turnover number and selectivity using said new catalyst.

DETAILED DESCRIPTION OF THE INVENTION

The present invention relates to the process for preparing hydroxyl aromatic hydrocarbons from aromatic hydrocarbon compounds by oxidation reaction.

This invention is characterized by the two-component heterogeneous catalyst used, one of which is zeolite catalyst containing Group VIII transition metal and alkylanthraquinone derivatives, and the other is zeolite catalyst containing transition metal with tetrahedral coordination geometry; that hydroxyl aromatic compounds are produced in a direct fashion by the introduction of hydrogen and oxygen under atmospheric pressure at a temperature of −10 to 60° C.

Detailed description of this invention is given below.

The catalyst for the preparation of hydrogen peroxide from hydrogen and oxygen has both a species to activate hydrogen and a chemical substance to transfer hydrogen effectively, permitting high efficiency in the production of hydrogen peroxide. If excess amount of reduced metal in catalyst exists, the activity of oxidation may be reduced due to the decomposition of hydrogen peroxide formed in solution. In addition, formed hydrogen peroxide needs appropriate catalyst which helps hydrogen peroxide to participate in the oxidation reaction effectively. It is preferable to use porous zeolite catalyst containing transition metal of tetrahedral coordination geometry such as titanium supported on zeolite framework. Generated hydrogen peroxide will lose the activity in oxidation reaction over catalyst in which transition metal like titanium is out of zeolite framework.

Zeolite employed in the present invention as a support is selected from Y, β, L type zeolite, MCM-41 and MCM-48 in the ratio of Si/Al being 1 to 160.

The suitable amount of Group VIII B transition metal, alkyl anthraquinone or its derivatives, and transition metal of tetrahedral coordination geometry in this new heterogeneous catalyst is 0.5 to 5.0 weight %, 0.5 to 4.0 weight % and 1.0 to 4.0 weight %, respectively.

If the amount of incorporated Group VIII B transition metal in two-component catalyst is under 0.5 weight %, hydrogen peroxide is produced in low concentration resulting in too low oxidation reactivity and in excess of 5.0 weight %, formed hydrogen peroxide is decomposed easily resulting in low conversion rate.

Furthermore, yield of hydrogen peroxide is closely related to the amount of incorporated alkyl anthraquinone and its derivatives which are hydrogen carriers in this process. Incorporation of alkyi anthraquinones in excess of 4.0% by weight in zeolites has been found to be difficult. Presence of alkyl anthraquinones below 0.5% by weight does not permit sufficient transfer hydrogen resulting in low hydrogen peroxide production. Said alkyl anthraquinone or its derivatives mean antluraquinone or substituted anthraquinone in which substituent is selected from the alkyl group containing 1 to 5 carbon atoms, carboxyl group and sulfonic group, more particularly, ethyl anthraquinone, butyl anthraquinone, amyl anthraquinone, anthraquinone-2-carboxylic acid, anthraquinone-1,5-disulfonic acid disodium salt.

Oxidation activity in this process depends on the concentration of transition metal with tetrahedral coordination geometry. If the amount is lower than 1.0 weight %, oxidation activity is too low while in excess of 4.0 weight %, results not only in difficulty to prepare optimal porous zeolite but also result in poor crystallinity causing limitation in the catalytic activity. Two-component catalyst in this invention comprises a porous catalyst containing Group VIII B transition metal and organic compounds, and a porous zeolite catalyst containing transition metal with tetrahedral coordination geometry. These two-component catalysts are prepared by appropriately mixing and utilizing the conventional processes.

Korea Patent Appln. No. 97-50302 discloses, in detail, the process for preparing a catalyst containing One of Group VIII B transition metal and a hydrogen carrier. Following is the example, for reference, of the preparation process for the catalyst containing palladium and 2-ethyl anthraquinone as well. Zeolite Y and $Pd(NH_3)_4Cl_2$ solution is stirred at 60° C. for 12 hours to permit ion-exchange of palladium, and washed thoroughly with distilled water until there is no detectable remains of $Pd(NH_3)_4Cl_2$. Pd-loaded catalyst is calcinated at 550° C. which is raised at a rate of 1° C. per min and subsequently reduced by treatment of hydrogen at 300° C. for 6 hours. Thereafter, a hydrogen carrier such as 2-ethylanthraquinone at the concentration of 0.1 to 0.5 M dissolved in benzene solution is mixed with fixed volume of dehydrated zeolite and then stirred at 60° C. for 3 days. Reaction mixture is washed with organic solvents such as benzene or acetone, using appropriate extraction device such as a Soxhlet extractor, and dried for 24 hours at a temperature 10° C. lower than the melting point of a hydrogen carrier to obtain the catalyst containing palladium and a hydrogen carrier.

Zeolite catalyst containing transition metal of tetrahedral coordination geometry, being the other component of the present catalyst, is prepared by means of the method of hydrothermal synthesis and secondary synthesis. Procedure for the preparation is the same as that described in the prior art [Ti-MCM-41: Stud. Surf. Sci. & Catal. 1994, 84, 68; TS-1: Appl. Catal. 1990, 57, L1; Ti-☐:Appl. Catal. A. 1995, 133, L185; Ti-ZSM-5: Appl. Catal. A. 1992, 84,141].

The two-component catalyst comprising a zeolite catalyst containing one of Group VIII B transition metal such as Pd, Pt, Au and Cu, and alkylanthraquinone derivatives and the other zeolite catalyst containing transition metal with tetrahedral coordination geometry produced by this invention is used for preparation of the hydroxyl aromatic compounds from aromatic hydrocarbon compounds by introducing hydrogen under atmospheric pressure at 20~60° C. and then by simultaneous contacting oxygen to produce hydrogen peroxide.

According to the oxidation reaction in this invention, the ratio of hydrogen to oxygen is very important factor to optimize the catalyst efficiency and oxidation activity. Hydrogen, in this reaction, requires to be improved by the metal supported on the catalyst, before it reacts with oxygen, to carry out optimal production of hydrogen peroxide. According to the present invention, optimum concentration ratio of oxygen and hydrogen is preferred in the range of 0.2 to 10. Efficiency to form hydrogen peroxide and oxidation activity is reduced when the concentration ratio of hydrogen and oxygen is out of said range.

When benzene is oxidized to phenol from hydrogen and oxygen using said two-component heterogeneous catalyst under atmospheric pressure at a temperature from 20 to 40° C. though depending on the reaction condition, turnover number based on titanium reaches 13.5 suggesting that catalyst performance is considerably improved compared to the results that have reported by other researchers.

The present invention will now be described in detail with reference to the following examples that by no means limit the scope of this invention.

EXAMPLE 1

The purpose of this example was to investigate the catalytic activity by means of hydroxylation of benzene. Reflux condenser, injection device for hydrogen and oxygen gas, and three-necked round flask reactor were used.

To 0.25 g of Y-zeolite containing 2-ethylanthraquinone and palladium, and 0.25 g of ZSM-5 zeolite containing titanium in a reactor were added 15 ml of benzene and then 15 ml of acetic acid. The reaction mixture was stirred to be homogenous. Hydrogen (diluted with nitrogen gas to 50%) and oxygen (diluted with nitrogen gas to 50%)($H_2/O_2=1$) were bubbled simultaneously into the reaction vessel at a flow rate of 16 ml/min at 60° C. for 5 hours. And then, product was analyzed by gas chromatography (Chrompack, CP9001, CPSIL5CB capillary column)

EXAMPLE 2

Performed in the manner of Example 1, except that the catalyst was 0.5 g of Y-zeolite containing 2-ethylanthraquinone and palladium, and 0.5 g of beta-zeolite containing titanium. Hydrogen and oxygen were introduced at a flow rate of 42 ml/min into the reaction vessel at 40° C. for 4 hours with 20 ml of benzene and 7 ml of acetic acid.

EXAMPLE 3

Performed in the manner of Example 2, except that the flow rate of hydrogen and oxygen ($H_2/O_2=0.5$) was 84 ml/min.

EXAMPLE 4

Performed in the manner of Example 1, except that hydrogen and oxygen were introduced at a flow rate of 10 ml/min at 50° C. for 4 hours.

EXAMPLE 5

Performed in the manner of Example 1, except that the catalyst was 0.1 g of Y-zeolite containing 2-ethylanthlaquinonie and palladium, and 0.1 g of Ti-containing silicalite (TS-1). Hydrogen and oxygen ($H_2/O_2=1$) were introduced to the reaction vessel at a flow rate of 16.8 ml/min at 50° C. for 6 hours with 6 ml of benzene and 6 ml of acetic acid.

EXAMPLE 6

Performed in the manner of Example 5, except that catalyst was 0.1 g of Y-zeolite containing 2-ethylanthraquinone and palladium, and 0.1 g of Ti-containing mesoporous material (Ti-MCM-41), 6 ml of benzene and 6 ml of acetic acid were supplied.

Comparative Example 1

Performed in the manner of Example 1, except that single component catalyst of Ti-containing silicalite (TS-1) was used instead of two-component catalyst.

Comparative Example 2

Performed in the manner of Example 1, except that single component catalyst of Y-zeolite was used containing 2-ethylanthraquinone and palladium instead of two-component catalyst.

Comparative Example 3

Performed in the manner of Example 1, except that catalyst was mesoporous material (Ti-MCM-41) containing titanium instead of two-component catalyst.

Comparative Example 4

Performed in the manner of Example 1, except that single component catalyst of Ti-ZSM-5 was used instead of two-component catalyst.

Comparative Example 5

Performed in the manner of Example 1, except that catalyst was 0.2 g of Y-zeolite containing 2-ethylanthraquinone and palladium, and 0.8 g of Ti-ZSM-5.

Comparative Example 6

Performed in the manner of Example 2, except that catalyst was 0.2 g of Y-zeolite containing 2-ethylanthraquinone and palladium, and 0.3 g of Ti-MCM-41.

Comparative Example 7

Performed in the manner of Example 5, except that catalyst was 0.1 g of Y-zeolite containing palladium and 0.1 g of TS-1 containing titanium.

Comparative Example 8

Performed in the manner of Example 6, except that catalyst was 0.1 g of Y-zeolite containing palladium and 0.1 g of Ti-MCM-41.

Table 1 shows the result of the reactions in which phenol is prepared from benzene by hydrogen and oxygen over the respective catalyst from examples 1 to 6 and comparative examples 1 to 8. No oxidation has occurred with hydrogen and oxygen in the reaction where zeolite catalyst (comparative examples 1, 3 and 4) containing only titanium. With single component catalyst containing palladium and organic substance (comparative example 2), benzene

| Examples | Type of catalyst (amount of active element, weight %) | Turnover number | | | Selectivity (%) |
|---|---|---|---|---|---|
| | | Titanium | Palladium | Organic compound | |
| Example 1 | *EPNY + Ti-ZSM-5 (Pd: 3.5, Ti: 2.0, EAQ: 1.8) | 2.3 | 1.0 | 6.4 | >97 |
| Example 2 | EPNY + Ti-β (Pd: 2.2, Ti: 1.8, EAQ: 2.0) | 2.0 | 1.3 | 5.4 | >97 |

-continued

| Examples | Type of catalyst (amount of active element, weight %) | Turnover number | | | Selectivity (%) |
| --- | --- | --- | --- | --- | --- |
| | | Titanium | Palladium | Organic compound | |
| Example 3 | EPNY + Ti-β (Pd: 1.8, Ti: 2.2, EAQ: 1.3) | 2.3 | 1.5 | 6.3 | >97 |
| Example 4 | EPNY + Ti-ZSM-5 (Pd: 4.0, Ti: 2.0, EAQ: 1.1) | 13.5 | 2.2 | 36.9 | >97 |
| Example 5 | EPNY +TS-1 (Pd: 2.0, Ti: 3.0, EAQ: 2.0) | 2.7 | 4.0 | 17.2 | 100 |
| Example 6 | EPNY + Ti-MCM-41 (Pd: 1.5, Ti: 2.5, EAQ: 0.8) | 1.23 | 1.0 | 4.5 | 100 |
| Comparative example 1 | TS-1 (Ti: 1.6) | 0 | — | — | 0 |
| Comparative example 2 | EPNY (Pd: 3.5, EAQ: 1.8) | — | 0.05 | — | >97 |
| Comparative example 3 | Ti-MCM-41 (Ti: 1.3) | 0 | — | — | 0 |
| Comparative example 4 | Ti-ZSM-5 (Ti: 1.5) | 0 | — | — | 0 |
| Comparative example 5 | EPNY + Ti-ZSM-5 (Pd: 3.0, Ti: 2.1, EAQ: 1.5) | 0.25 | 0.08 | 0.30 | >95 |
| Comparative example 6 | EPNY + Ti-MCM-41 (Pd: 3.0, Ti: 2.0, EAQ: 0.9) | 1.83 | 2.06 | 8.94 | 56 |
| Comparative example 7 | PNY + TS-1 (Pd: 2.0, Ti: 3.0) | 0.6 | 0.9 | — | 95 |
| Comparative example 8 | PNY + MCM-41 (Pd: 1.5, Ti: 2.5) | 0.3 | 0.2 | — | 95 |

Turnover number: moles of phenol prepared by 1 mol of active species (titanium, palladium, encapsulated organic compound and etc.) during oxidation
*EPNY: NaY zeolite supported with 2-ethylanthraquinone and palladium was oxidized to some extent, but production of phenol was very poor. On the other hand, reaction by two-component catalyst which contains Pd, Ti and organic material in the controlled manner shows highly improved turnover number. But the reaction activity was significantly sensitive to the amount of incorporated metal, the method of incorporation and relative composition of two-component catalyst. Oxidation activity of catalyst is higher in the catalyst which contains ethylanthraquinone as hydrogen carrier than the catalyst which does not, where turnover number is increased by 4 to 5 folds in the experiment of examples 5 to 6 compared to that in the comparative examples 7 to 8. The catalyst in which oxidation state, dispersion state, amount of incorporated palladium and coordination state of titanium were properly controlled exhibited highly improved oxidation activity and selectivity (example 1 to 6) compared to the catalyst which were not (comparative example 5 and 6).

According to the present invention, if the amount of incorporated palladium is too much, hydrogen peroxide resulting from the reaction is liable to be decomposed. If the oxidation state of palladium is not in good control, activation of hydrogen is poor, resulting production of hydrogen peroxide is small, and finally turnover number of phenol is low. In addition, incorporated titanium should be tetrahedral coordinated in the zeolite framework to be effectively utilized for oxidation. Furthermore, oxidation efficiency of catalyst can be improved in the presence of hydrogen transfer organic substance as well as palladium in the catalyst.

Two-component catalyst which meets all the said demands alone are able to oxidize benzene to phenol under mild condition by direct introduction of oxygen and hydrogen.

What is claimed is:

1. A process for direct hydroxylation of an aromatic compound, comprising contacting an aromatic compound with at least one two-component heterogeneous catalyst comprising at least one zeolite catalyst which contains at least one Group VIII B transition metal and at least one alkyl anthraquinone or its derivative, and at least one zeolite catalyst which contains at least one transition metal with tetrhedral coordination geometry, wherein hydroxylation is performed using hydrogen and oxygen under atmospheric pressure and at a temperature ranging from −10 to 60° C.

2. The process of claim 1, wherein said at least one alkyl anthraquinone or its derivative is chosen from ethyl anthraquinone, butyl anthraquinone, amyl anthraquinone, anthraquinone-2-carboxylic acid, and anthraquinone-1,5-disulfonic acid disodium salt.

3. The process of claim 1, wherein said at least one zeolite catalyst is chosen from Y-zeolites, β-zeolites, L-zeolites, MCM-41 zeolites, and MCM-48 zeolites in which ratio of Si/Al ranges from 1 to 160.

4. The process of claim 1, wherein said at least one Group VIII B transition metal is chosen from Au, Pd, Cu, and Pt.

5. The process of claim 1, wherein said at least one transition metal with tetrahedral coordination geometry is chosen from vandium and titanium.

6. The process of claim 1, wherein said at least one two-component heterogeneous catalyst contains said at least one Group VIII B transition metal, said at least one alkyl anthraquinone or its derivative, and said at least one transition metal with tetrahedral coordination geometry in an amount ranging from 0.5 to 5.0 weight %, 0.5 to 4.0 weight %, and 1.0 to 4.0 weight %, respectively.

7. The process of claim 1, wherein the concentration ratio of oxygen and hydrogen ranges from 0.2 to 10.

8. A process for direct hydroxylation of an aromatic compound, comprising contacting an aromatic compound with at least one two-component heterogeneous catalyst comprising zeolite catalyst which contains at least one Group VIII B transition metal and at least one alkyl anthraquinone or its derivative, and at least one zeolite catalyst which contains tin with tetrhedral coordination geometry, wherein hydroxylation is performed using hydrogen and oxygen under atmospheric pressure and at a temperature ranging from −10 to 60° C.

9. The process of claim 8, wherein said at least one alkyl anthraquinone or its derivative is chosen from ethyl anthraquinone, butyl anthraquinone, amyl anthraquinone, anthraquinone-2-carboxylic acid, and anthraquinone-1,5-disulfonic acid disodium salt.

10. The process of claim 8, wherein said at least one zeolite catalyst is chosen from Y-zeolites, β-zeolites, L-zeolites, MCM-41 zeolites, and MCM-48 zeolites in which ratio of Si/Al ranges from 1 to 160.

11. The process of claim 8, wherein said at least one Group VIII B transition metal is chosen from Au, Pd, Cu, and Pt.

12. The process of claim 8, wherein said at least one two-component heterogeneous catalyst contains said at least one Group VIII B transition metal, said at least one alkyl anthraquinone or its derivative, and said tin with tetrahedral coordination geometry in an amount ranging from 0.5 to 5.0 weight %, 0.5 to 4.0 weight %, and 1.0 to 4.0 weight %, respectively.

13. The process of claim 8, wherein the concentration ratio of oxygen and hydrogen ranges from 0.2 to 10.

* * * * *